(12) United States Patent
Tornier et al.

(10) Patent No.: US 7,678,150 B2
(45) Date of Patent: Mar. 16, 2010

(54) TOTAL SHOULDER PROSTHESIS OF AN INVERTED TYPE

(75) Inventors: Alain Tornier, Saint Ismier (FR); Gilles Walch, Lyons (FR); Pascal Boileau, Nice (FR)

(73) Assignee: Tornier SAS, Saint Ismier (FR)

( * ) Notice: Subject to any disclaimer, the term of this patent is extended or adjusted under 35 U.S.C. 154(b) by 0 days.

(21) Appl. No.: 11/151,658

(22) Filed: Jun. 14, 2005

(65) Prior Publication Data

US 2005/0278033 A1 Dec. 15, 2005

Related U.S. Application Data

(60) Provisional application No. 60/579,257, filed on Jun. 15, 2004.

(30) Foreign Application Priority Data

Jun. 15, 2004 (FR) .................................. 04 06472

(51) Int. Cl.
*A61F 2/40* (2006.01)
(52) U.S. Cl. .................................. 623/19.13
(58) Field of Classification Search ... 623/19.11–19.14, 623/18.11
See application file for complete search history.

(56) References Cited

U.S. PATENT DOCUMENTS

| | | | |
|---|---|---|---|
| 3,694,820 A * | 10/1972 | Scales et al. ............. | 623/19.12 |
| 3,815,157 A | 6/1974 | Skorecki et al. | |
| 3,842,442 A | 10/1974 | Kolbel | |
| 3,864,758 A | 2/1975 | Yakich | |
| 3,869,730 A | 3/1975 | Skobel | |
| 3,916,451 A | 11/1975 | Buechel et al. | |
| 3,978,528 A | 9/1976 | Crep | |
| 3,979,778 A | 9/1976 | Stroot | |
| 3,992,726 A | 11/1976 | Freeman et al. | |
| 4,003,095 A | 1/1977 | Gristina | |
| 4,030,143 A | 6/1977 | Elloy et al. | |
| 4,040,131 A | 8/1977 | Gristina | |
| 4,054,955 A | 10/1977 | Seppo | |
| 4,135,517 A | 1/1979 | Reale | |

(Continued)

FOREIGN PATENT DOCUMENTS

CH 426096 12/1966

(Continued)

OTHER PUBLICATIONS

Orthopedics Clinics of North America, vol. 6, Nr. 2, Apr. 1975, "Total Glenohumeral Joint Replacement", Fenlin, JM.

(Continued)

*Primary Examiner*—Corrine McDermott
*Assistant Examiner*—Cheryl Miller
(74) *Attorney, Agent, or Firm*—Faegre & Benson LLP (57) ABSTRACT

A total shoulder prosthesis includes a glenoidal component a substantially hemispherical convex articular surface and of which a center of curvature is adapted, when the prosthesis is implanted, to be located in the glenoid cavity or in the immediate vicinity thereof, and a humeral component defining a concave articular surface adapted to cooperate with the convex articular surface of the glenoidal component. The concave humeral articular surface is defined by a metallic part of the humeral component to thereby reduce a space requirement of the prosthesis.

27 Claims, 2 Drawing Sheets

U.S. PATENT DOCUMENTS

| | | |
|---|---|---|
| 4,179,758 A | 12/1979 | Gristina |
| 4,206,517 A | 6/1980 | Pappas et al. |
| 4,261,062 A | 4/1981 | Amstutz et al. |
| 4,550,450 A | 11/1985 | Kinnett |
| 4,693,723 A | 9/1987 | Gabard |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazerri et al. |
| 5,032,132 A | 7/1991 | Matsen, III et al. |
| 5,080,673 A | 1/1992 | Burkhead et al. |
| 5,080,685 A | 1/1992 | Bolesky et al. |
| 5,127,920 A | 7/1992 | MacArthur |
| 5,135,529 A | 8/1992 | Paxson et al. |
| 5,163,961 A | 11/1992 | Harwin |
| 5,171,289 A | 12/1992 | Tornier |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,261,914 A | 11/1993 | Warren |
| 5,314,479 A | 5/1994 | Rockwood, Jr. et al. |
| 5,314,485 A | 5/1994 | Judet |
| 5,314,487 A | 5/1994 | Schryver et al. |
| 5,326,359 A | 7/1994 | Oudard |
| 5,330,531 A | 7/1994 | Cappana |
| 5,358,526 A | 10/1994 | Tornier |
| 5,383,936 A | 1/1995 | Kubein-Meesenburg et al. |
| 5,405,399 A | 4/1995 | Tornier |
| 5,425,779 A | 6/1995 | Schlosser |
| 5,429,639 A | 7/1995 | Judet |
| 5,443,519 A | 8/1995 | Averill et al. |
| 5,458,650 A | 10/1995 | Carrett et al. |
| 5,462,563 A | 10/1995 | Shearer et al. |
| 5,505,731 A | 4/1996 | Tornier |
| 5,507,817 A | 4/1996 | Craig et al. |
| 5,507,818 A | 4/1996 | McLaughlin |
| 5,507,824 A | 4/1996 | Lennox |
| 5,549,682 A | 8/1996 | Roy |
| 5,580,352 A | 12/1996 | Sekel |
| 5,591,168 A | 1/1997 | Judet et al. |
| 5,662,651 A | 9/1997 | Tornier et al. |
| 5,676,702 A | 10/1997 | Ratron |
| 5,702,447 A | 12/1997 | Walch et al. |
| 5,702,457 A | 12/1997 | Walch et al. |
| 5,702,478 A | 12/1997 | Tornier |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,807 A | 5/1998 | Anstaett et al. |
| 5,766,256 A | 6/1998 | Oudard et al. |
| 5,800,551 A | 9/1998 | Williamson et al. |
| 5,824,106 A | 10/1998 | Fournol |
| 5,879,395 A | 3/1999 | Tornier et al. |
| 5,879,405 A | 3/1999 | Ries et al. |
| 5,902,340 A | 5/1999 | White et al. |
| 5,910,171 A | 6/1999 | Kummer et al. |
| 5,928,285 A | 7/1999 | Bigliani |
| 5,944,758 A | 8/1999 | Mansat et al. |
| 5,961,555 A | 10/1999 | Huebner |
| 5,984,927 A | 11/1999 | Wenstrom, Jr. et al. |
| 6,015,437 A | 1/2000 | Stossel |
| 6,033,439 A | 3/2000 | Camino et al. |
| 6,045,582 A | 4/2000 | Prybyla |
| 6,045,583 A | 4/2000 | Gross et al. |
| 6,102,953 A | 8/2000 | Huebner |
| 6,129,764 A | 10/2000 | Servidio |
| 6,162,254 A | 12/2000 | Timoteo |
| 6,165,224 A | 12/2000 | Tornier |
| 6,168,629 B1 | 1/2001 | Timoteo |
| 6,171,341 B1 | 1/2001 | Boileau et al. |
| 6,183,519 B1 | 2/2001 | Bonnin et al. |
| 6,197,062 B1 | 3/2001 | Fenlin |
| 6,197,063 B1 | 3/2001 | Dews |
| 6,203,575 B1 | 3/2001 | Farey |
| 6,206,925 B1 | 3/2001 | Tornier |
| 6,228,120 B1 | 5/2001 | Leonard et al. |
| 6,267,767 B1 | 7/2001 | Stroble et al. |
| 6,283,999 B1 | 9/2001 | Rockwood, Jr. |
| 6,299,646 B1 | 10/2001 | Chambat et al. |
| 6,312,467 B1 | 11/2001 | McGee |
| 6,328,758 B1 | 12/2001 | Tornier et al. |
| 6,334,874 B1 | 1/2002 | Tornier et al. |
| 6,364,910 B1 | 4/2002 | Schultz et al. |
| 6,368,352 B1 | 4/2002 | Camino et al. |
| 6,368,353 B1 * | 4/2002 | Arcand .................... 623/19.13 |
| 6,379,387 B1 | 4/2002 | Tornier |
| 6,398,812 B1 | 6/2002 | Masini |
| 6,406,495 B1 | 6/2002 | Schoch |
| 6,406,496 B1 | 6/2002 | Rüter |
| 6,436,144 B1 | 8/2002 | Ahrens |
| 6,436,147 B1 | 8/2002 | Zweymuller |
| 6,454,809 B1 | 9/2002 | Tornier |
| 6,458,136 B1 | 10/2002 | Allard et al. |
| 6,475,243 B1 | 11/2002 | Sheldon et al. |
| 6,488,712 B1 | 12/2002 | Tornier et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,514,287 B2 | 2/2003 | Ondrla et al. |
| 6,520,994 B2 | 2/2003 | Nogarin |
| 6,530,957 B1 | 3/2003 | Jack |
| 6,540,770 B1 | 4/2003 | Tornier et al. |
| 6,558,425 B2 | 5/2003 | Rockwood |
| 6,569,202 B2 | 5/2003 | Whiteside |
| 6,582,469 B1 | 6/2003 | Tornier |
| 6,589,281 B2 | 7/2003 | Hyde, Jr. |
| 6,599,295 B1 | 7/2003 | Tornier et al. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,736,851 B2 | 5/2004 | Maroney et al. |
| 6,746,487 B2 | 6/2004 | Scifert et al. |
| 6,749,637 B1 | 6/2004 | Bahler |
| 6,761,740 B2 | 7/2004 | Tornier |
| 6,767,368 B2 | 7/2004 | Tornier |
| 6,780,190 B2 | 8/2004 | Maroney |
| 6,783,549 B1 | 8/2004 | Stone et al. |
| 6,790,234 B1 | 9/2004 | Frankle |
| 6,802,864 B2 | 10/2004 | Tornier |
| 6,824,567 B2 | 11/2004 | Tornier et al. |
| 6,863,690 B2 | 3/2005 | Ball et al. |
| 6,875,234 B2 | 4/2005 | Lipman et al. |
| 6,890,357 B2 | 5/2005 | Tornier |
| 6,890,358 B2 | 5/2005 | Ball et al. |
| 6,942,699 B2 | 9/2005 | Stone et al. |
| 6,953,478 B2 * | 10/2005 | Bouttens et al. .......... 623/19.11 |
| 6,969,406 B2 | 11/2005 | Tornier |
| 7,011,686 B2 | 3/2006 | Ball et al. |
| 7,033,396 B2 | 4/2006 | Tornier |
| 7,166,132 B2 | 1/2007 | Callaway et al. |
| 7,175,663 B1 * | 2/2007 | Stone ...................... 623/19.13 |
| 7,195,645 B2 | 3/2007 | Disilvestro et al. |
| 7,238,207 B2 | 7/2007 | Blatter et al. |
| 7,238,208 B2 | 7/2007 | Camino et al. |
| 7,297,163 B2 | 11/2007 | Huebner |

| | | |
|---|---|---|
| 7,338,498 B2 | 3/2008 | Long et al. |
| 7,338,528 B2 | 3/2008 | Stone et al. |
| 2001/0047210 A1 | 11/2001 | Wolf |
| 2001/0049561 A1 | 12/2001 | Dews et al. |
| 2002/0138148 A1 | 9/2002 | Hyde, Jr. |
| 2002/0143402 A1 | 10/2002 | Steinberg |
| 2002/0151982 A1 | 10/2002 | Masini |
| 2003/0009170 A1 | 1/2003 | Tornier |
| 2003/0009171 A1 | 1/2003 | Tornier |
| 2003/0028198 A1 | 2/2003 | Tornier et al. |
| 2003/0074072 A1 | 4/2003 | Errico et al. |
| 2003/0097183 A1 | 5/2003 | Rauscher et al. |
| 2003/0114933 A1 | 6/2003 | Bouttens et al. |
| 2003/0149485 A1 | 8/2003 | Tornier |
| 2003/0158605 A1 | 8/2003 | Tornier |
| 2004/0002765 A1 | 1/2004 | Maroney et al. |
| 2004/0006392 A1 | 1/2004 | Grusin et al. |
| 2004/0030394 A1 | 2/2004 | Horber |
| 2004/0034431 A1 | 2/2004 | Maroney et al. |
| 2004/0039449 A1 | 2/2004 | Tornier |
| 2004/0064189 A1 | 4/2004 | Maroney et al. |
| 2004/0064190 A1 | 4/2004 | Ball et al. |
| 2004/0133276 A1 | 7/2004 | Lang et al. |
| 2004/0134821 A1 | 7/2004 | Tornier |
| 2004/0138754 A1 | 7/2004 | Lang et al. |
| 2004/0148033 A1* | 7/2004 | Schroeder ............ 623/23.53 |
| 2004/0153161 A1* | 8/2004 | Stone et al. ............ 623/19.14 |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210220 A1 | 10/2004 | Tornier |
| 2004/0210317 A1 | 10/2004 | Maroney et al. |
| 2004/0215200 A1 | 10/2004 | Tornier et al. |
| 2004/0220673 A1 | 11/2004 | Prla |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0267370 A1 | 12/2004 | Ondria |
| 2005/0008672 A1 | 1/2005 | Winterbottom et al. |
| 2005/0015154 A1 | 1/2005 | Lindsey et al. |
| 2005/0043805 A1 | 2/2005 | Chudik |
| 2005/0049709 A1 | 3/2005 | Tornier |
| 2005/0055102 A1 | 3/2005 | Tornier et al. |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0203536 A1 | 9/2005 | Laffargue et al. |
| 2005/0209700 A1 | 9/2005 | Rockwood et al. |
| 2005/0216092 A1 | 9/2005 | Marik et al. |
| 2005/0251263 A1 | 11/2005 | Forrer et al. |
| 2005/0256584 A1 | 11/2005 | Farrar |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0015185 A1 | 1/2006 | Chambat et al. |
| 2006/0020344 A1 | 1/2006 | Schultz et al. |
| 2006/0030946 A1 | 2/2006 | Ball et al. |
| 2006/0173457 A1 | 8/2006 | Tornier |
| 2006/0235538 A1 | 10/2006 | Rochetin et al. |
| 2006/0241775 A1 | 10/2006 | Buss |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2007/0250174 A1 | 10/2007 | Tornier et al. |

FOREIGN PATENT DOCUMENTS

| | | |
|---|---|---|
| CH | 507704 | 5/1971 |
| DE | 19509037 | 9/1996 |
| DE | 19630298 | 1/1998 |
| EP | 0257359 | 3/1988 |
| EP | 0299889 | 1/1989 |
| EP | 0524857 | 1/1993 |
| EP | 549460 | 6/1993 |
| EP | 0599429 | 6/1994 |
| EP | 617934 | 10/1994 |
| EP | 0664108 | 7/1995 |
| EP | 0679375 | 11/1995 |
| EP | 0712617 | 5/1996 |
| EP | 715836 | 6/1996 |
| EP | 0797694 | 10/1997 |
| EP | 0807426 | 11/1997 |
| EP | 0809986 | 12/1997 |
| EP | 0864306 | 9/1998 |
| EP | 0903127 | 3/1999 |
| EP | 903128 | 3/1999 |
| EP | 927548 | 7/1999 |
| EP | 1062923 | 12/2000 |
| EP | 1064890 | 1/2001 |
| EP | 1195149 | 4/2002 |
| EP | 1380274 | 1/2004 |
| EP | 1402854 | 3/2004 |
| FR | 2248820 | 10/1973 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2 704 747 | * 11/1994 |
| FR | 2721200 | 12/1995 |
| FR | 2726994 | 5/1996 |
| FR | 2737107 | 1/1997 |
| FR | 2835425 | 8/2003 |
| FR | 2836039 | 8/2003 |
| SU | 749392 | 7/1980 |
| WO | WO 91/07932 | 6/1991 |
| WO | WO 93/09733 | 5/1993 |
| WO | WO 96/17553 | 6/1996 |
| WO | WO 98/46172 | 10/1998 |
| WO | WO 99/49792 | 10/1999 |
| WO | WO 99/65413 | 12/1999 |
| WO | WO 00/15154 | 3/2000 |
| WO | WO 00/41653 | 7/2000 |
| WO | WO 01/47442 | 7/2001 |
| WO | WO 02/39931 | 5/2002 |
| WO | WO 02/39933 | 5/2002 |
| WO | WO 02/067821 | 9/2002 |
| WO | WO 03/005933 | 1/2003 |
| WO | WO03/094806 | 11/2003 |
| WO | WO 2007/109319 | 2/2007 |
| WO | WO 2007/109291 | 9/2007 |
| WO | WO 2007/109340 | 9/2007 |

OTHER PUBLICATIONS

Rochetin, U.S. Appl. No. 11/194,452, entitled "Patellar Retractor and Method of Surgical Procedure on Knee," filed Aug. 2, 2005.

Rochetin et al., U.S. Appl. No. 11/401,415, entitled "Surgical Apparatus for Implantation of a Partial or Total," filed Apr. 11, 2006.

Rochetin, U.S. Appl. No. 11/670,274, entitled "Offset Stem Tibial Implantation," filed Feb. 1, 2007.

Ratron et al., U.S. Appl. No. 11/626,735, entitled "Surgical Insturmentation Kit for Inserting an Ankle Prothesis," filed Jan. 1, 2007.

Boileau et al., U.S. Appl. No. 12/020,913, entitled "Method and Apparatus for Fitting a Shoulder Prosthesis" filed Jan. 28, 2008.

John M. Fenlin Jr., M.D., Symposium on Surgery of the Shoulder, "Total Glenohumeral Joint Replacement," *Orthopedic Clinics of North America*, vol. 6, No. 2, Apr. 1975, pp. 565-583.

"Aequalis-Fracture Suture Technique in 5 Steps," Tornier, Inc.

"Aequalis-Fracture Shoulder Prosthesis—Surgical Technique," Tornier, Inc.

"Aequalis® Press-Fit Shoulder Prosthesis—Surgical Technique," Tornier, Inc.

"Anatomical Shoulder™—Cemented Shoulder Prosthesis Product Information and Surgical Technique," Sulzer Medica, 2000.

"Anatomical Shoulder™ System Surgical Technique—Removable head option for improved surgical results," Zimmer, Inc., 2004.

Bigliani/Flatow®—The Complete Shoulder Solution, 4-Part Fracture of the Humerus Surgical Technique, Zimmer, Inc., 2000.

"Bio-Modular® / Bi-Polar Shoulder Arthroplasty," Biomet, Inc., 1997.

"Bio-Modular® Choice, Shoulder System," Biomet Orthopedics, Inc., 2004.

"Bio-Modular Total Shoulder Surgical Technique," Biomet Orthopedics, Inc., 2001.

"Copeland™ Humeral Resurfacing Head," Biomet Orthopedics, Inc., 2001.

"Global C.A.P.™ Surgical technique, resurfacing humeral head implant," DePuy International, Ltd., 2004.

Boileau, et al. "Adaptability and modularity of shoulder prostheses," *Maitrise Orthopédique*, http://www.maitrise-orthop.com/corpusmaitri/orthopaedic/prothese_epaule_orthop/boileau_us.shtml, Jan. 3, 2006.

Boileau, et al. "Arthroscopic Repair of Full-Thickness Tears of the Supraspinatus: Does the tendon really heal?," *The Journal of Bone and Joint Surgery, Inc.*, pp. 1229-1240, 2005.

"Design Rationale," Latitude®.

Klein, Travis J., et al. "Mechanically favorable bone remodeling in rotator cuff arthropathy patients with good function," *Minneapolis Sports Medicine Center and University of Minnesota*.

Mansat, Michel, "Neer 3™, Surgical Technique for Fractrures," Smith & Nephew, 2000.

Molé, M.D., et al., "Aequalis-Reversed™ Shoulder Prosthesis, Surgical Technique," Tornier, Inc.

Nicholson, Gregory P., "Arthroplasty and Rotator Cuff Deficiency," Chapter 7, pp. 149-166.

"Offset Head, Bio-Modular® Total Shoulder," Biomet, Inc. 2000.

"The Foundation® Total Shoulder System," Encore Surgical.

"The Townley Modular Shoulder, Design by Reason," Biopro, Inc.

Zimmer® Bigliani/Flatow®—The Complete Shoulder Solution, Total Shoulder Arthroplasty Surgical Technique, Zimmer, Inc., 2003.

"Zimmer® Shoulder Retractors," Zimmer, Inc., 2000.

"Anatomic Glenoid, Surgical Technique," Smith & Nephew, 2000.

"Anatomical Shoulder™ System—The new removable head option," Zimmer Inc., 2004.

"Delta CTA™ Reverse Shoulder Prosthesis—Surgical Technique," DePuy International, Ltd., 2004.

Cofield, M.D., Robert H. "Cofield$^2$ Total Shoulder System, Surgical Technique," Smith & Nephew, 1997.

"Aequalis®-Glenoid Keeled and Pegged—Surgical Technique," Tornier, Inc.

"Bigliani/Flatow®—The Complete Shoulder Solution, Designed by Shoulder Surgeons for Shoulder Surgery," Zimmer, Inc., 2001.

"Tornier Surgical Technique Addendum, Tornier Aequalis® Reversed Hemi-Adaptor Technique," Tornier, Inc., Oct. 8, 2005.

"Tornier Surgical Technique Addendum, Aequalis® Reversed Shoulder Polyethylene Insert," Tornier, Inc., Oct. 8, 2005.

Beuchel M.D., Frederick F. "Beuchel-Pappas™ Modular Salvage Shoulder System," Endotec, Inc., 2000.

Beuchel M.D., Frederick F. "Beuchel-Pappas™ Resurfacing Shoulder System," Endotec, Inc., 2000.

Beuchel M.D., Frederick F. "Beuchel-Pappas™ Total Shoulder System," Endotec, Inc., 2000.

Hertel M.D., PD, Ralph. "Technical considerations for implantation of EPOCA glenoid components (Leseprobe)," *Epoca Newsletter*, May 14, 2001.

Apoil, André "A Condyle for the Rotator Cuff Muscles, the total shoulder prosthesis," Aesculap®, 1994.

"Tornier Aequalis® Reversed 2 Prong Capsular Retractor," Tornier, Inc., Oct. 8, 2005.

"Tornier Aequalis® Reversed Shoulder G2 Baseplate," Tornier, Inc., Oct. 8, 2005.

* cited by examiner

TOTAL SHOULDER PROSTHESIS OF AN INVERTED TYPE

BACKGROUND OF THE INVENTION

1. Field of the Invention

The present invention relates to a shoulder prosthesis and, more specifically, to a shoulder prosthesis whose compactness can be improved with respect to those of the state of the art.

2. Brief Description of the Related Art

In the domain of shoulder prostheses, it is known, for example from EP-A-0 299 889, to constitute a so-called "inverted" prosthesis in which a convex articular surface implanted within a glenoid cavity and a concave articular surface implanted within a humerus, cooperate in order to recreate a joint at the shoulder, with a center of rotation located in the glenoid cavity. In this type of prosthesis, the convex articular surface is often made of metal, while a cup made of synthetic material, for example polyethylene, is shaped so as to create the concave humeral surface of articulation. In order to withstand the efforts to which it is subjected, such a cup must have a relatively great thickness, this causing a lateral space requirement of the prosthesis which may sometimes inhibit the patient, particularly during movements of abduction.

It is a more particular object of the present invention to overcome these drawbacks by proposing a novel total shoulder prosthesis of inverted type in which there is less risk of the lateral space requirement inhibiting the patient than the prostheses of the state of the art.

SUMMARY OF THE INVENTION

In that spirit, the invention relates to a total shoulder prosthesis comprising a glenoidal component, defining a substantially hemispherical convex articular surface of which the center of curvature is located in the glenoid cavity or in the immediate vicinity of the glenoid cavity, and a humeral component defining a concave articular surface adapted to cooperate with the convex articular surface of the glenoidal component, characterized in that the concave articular surface is defined by a metallic part of the humeral component.

With the invention, the lateral space requirement for implant of the prosthesis can be optimized, while conserving the functional character of the humeral articular surface.

According to advantageous but non-obligatory aspects of the invention, a total shoulder prosthesis of inverted type may incorporate one or more of the characteristics set forth below, taken in any technically admissible combination.

The convex articular surface is defined in a metallic part of the glenoidal component. Surprisingly, a prosthesis of inverted type in which the two articular surfaces are made of metal has proved to allow a patient to move easily, while the fact of dispensing with polyethylene allows a better compactness of the prosthesis, particularly a reduction in its lateral space requirement.

The metallic parts in which the articular surfaces are formed are made of titanium or a chromium-cobalt alloy.

According to a first embodiment, the humeral component comprises a one-piece metaphyseal part which defines the concave articular surface.

According to another embodiment, the humeral component comprises a two-piece metaphyseal part formed by a body on which is mounted a metallic insert defining the concave articular surface. In this case, the insert is advantageously immobilized on the body by cooperation of shapes. In addition, this body may be provided to be adapted to receive different implants which define articular surfaces which are different and/or positioned differently with respect to the body, this making it possible to adapt, to a certain extent, the prosthesis to its site of implantation.

Whatever the embodiment considered, the metaphyseal part of the humeral component may be in one piece with, or added on, a stem for anchorage of the component in the humerus.

The humeral component is entirely metallic.

BRIEF DESCRIPTION OF THE DRAWINGS

The invention will be more readily understood and other advantages thereof will appear more clearly in the light of the following description of two forms of embodiment of a prosthesis in accordance with its principle, given solely by way of example and made with reference to the accompanying drawings, in which.

DESCRIPTION OF PREFERRED EMBODIMENTS

Figure 1:
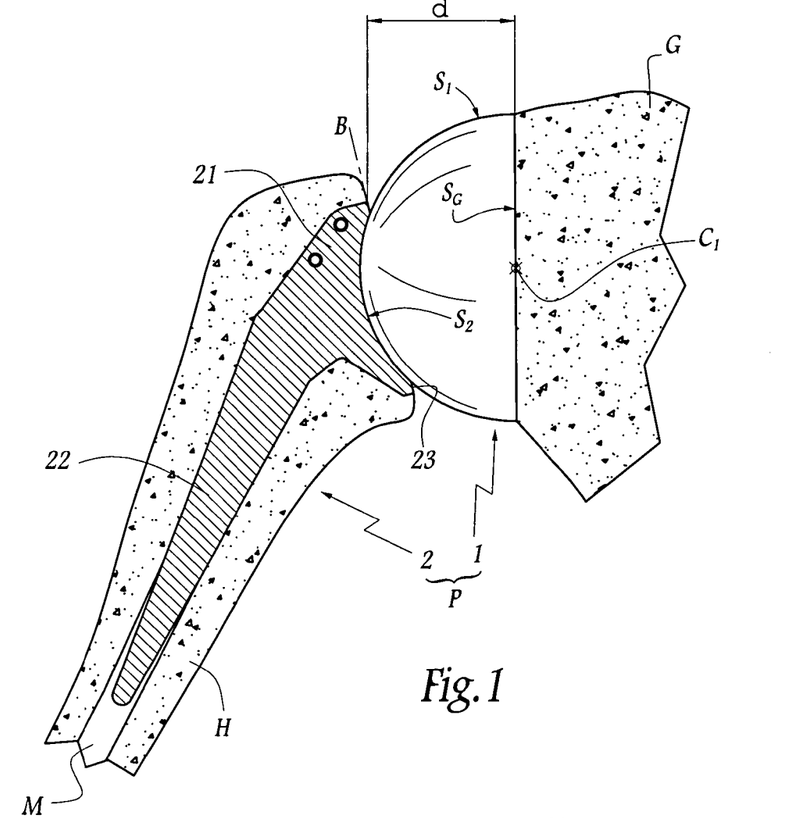
FIG. 1 schematically shows a prosthesis according to the invention implanted in a patient's shoulder.

Referring now to the drawings, the prosthesis P shown in FIG. 1 comprises a glenoidal component 1 which defines a convex articular surface $S_1$ of globally hemispherical shape and of which the center of curvature $C_1$ is located at the rear face of the component 1, i.e. at the milled surface $S_G$ of the glenoid cavity. As is more particularly visible in FIG. 3, the component 1 comprises a base 11 provided with an anchoring stem 12 and intended to be fixed on the glenoid cavity G by means of a plurality of screws (not shown). A metallic head 13 is provided to be mounted on the base 11 and shaped to define the surface $S_1$. This glenoidal component may, for example, be in accordance with the technical teaching of French Patent 2 835 425.

Figure 2:
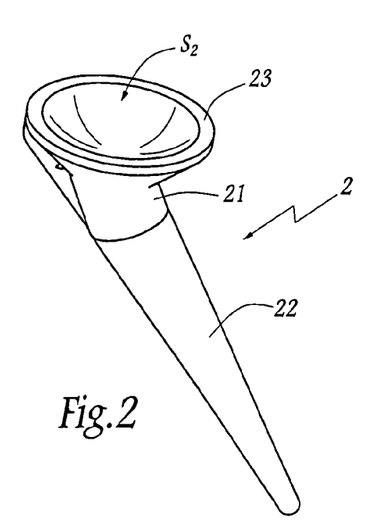
FIG. 2 is a view in perspective of the humeral component of the prosthesis of FIG. 1.

The prosthesis P also comprises a humeral component 2 which is also metallic. The component 2 comprises a metaphyseal part 21 in one piece with a stem 22 for anchoring in the medullary canal M of the humerus H. The part 21 is hollowed out by machining and defines a concave surface $S_2$ in the form of a portion of sphere of radius substantially equal to that of the surface $S_1$.

The surface $S_2$ is bordered by an annular and circular edge 23.

When the prosthesis is implanted, as shown in FIG. 1, where the component 2 is shown in section while the component 1 is shown in outside view in order to render the drawing clearer, the surfaces $S_1$ and $S_2$ are in surface abutment against each other, this allowing the different shoulder movements which are sought after.

Taking into account the fact that the surface $S_2$ is formed by the part 21 itself, the distance d between the resectioned surface $S_G$ of the glenoid cavity and the cut edge B of the resectioned humerus H is relatively small compared to the same distance for a known prosthesis.

Figure 3:
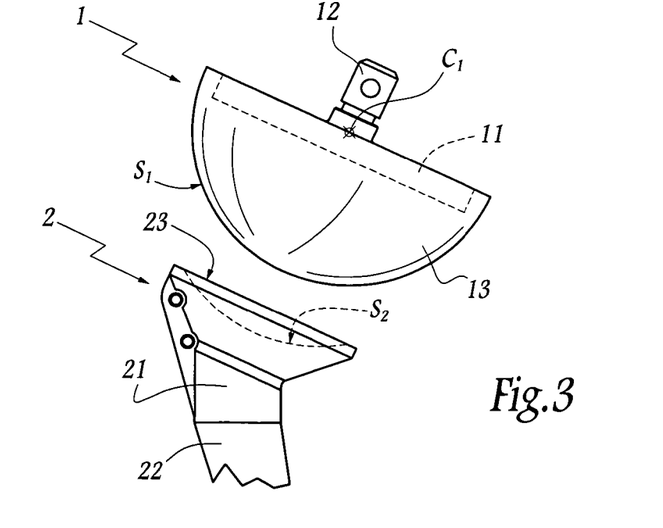
FIG. 3 is a side view of a part of the humeral component and of the glenoidal component of the prosthesis of FIG. 1, in configuration separated from each other.

The part 13 and the component 2 are advantageously made of a bio-compatible metal, for example titanium or an alloy based on chromium-cobalt.

According to an advantageous variant of the invention, the surface $S_2$ is not necessarily centered in the metaphyseal part 21. For example, the component 2 may be selected from a set of components of which the surfaces $S_2$ are more or less eccentric with respect to their respective metaphyseal parts.

Figure 4:
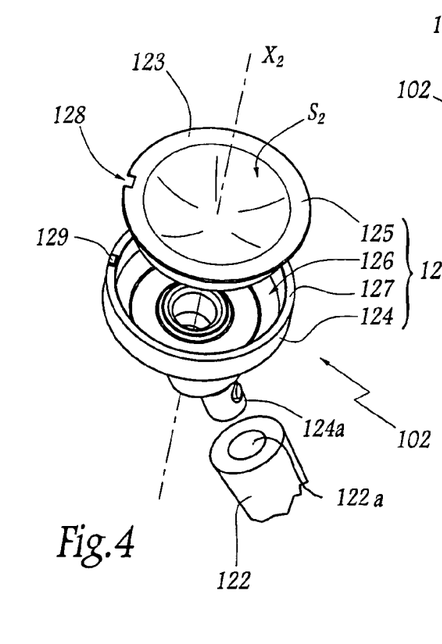
FIG. 4 is a view in perspective of the humeral component of a prosthesis according to a second form of embodiment of the invention.
Figure 5:
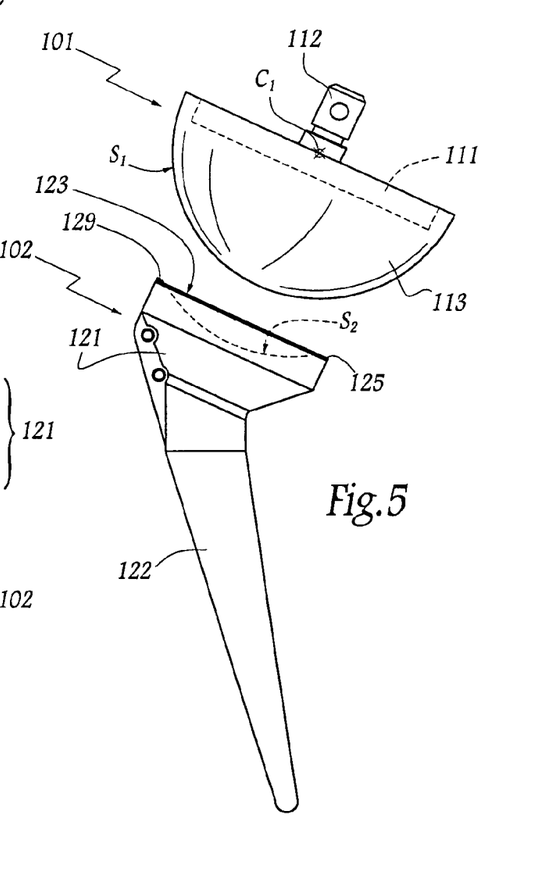
FIG. 5 is a view similar to FIG. 3 for the prosthesis of which the humeral element is shown in FIG. 4.

In the second form of embodiment of the invention shown in FIGS. 4 and 5, elements similar to those of the first embodiment bear identical references increased by 100. The glenoidal component 101 of this embodiment also comprises a base 111 of which the stem 112 allows anchoring in the glenoid cavity as well as a metallic head 113 defining a hemispherical, convex articular surface $S_1$.

The humeral component 102 comprises a metaphyseal part 121 constituted by a body 124 and an insert 125, both metallic. The insert and the body are advantageously made of the same metal or metallic alloy, for example titanium or an alloy based on chromium-cobalt.

The insert 125 is intended to be immobilized on the body 124 by cooperation of shapes, being partially engaged in the inner volume 126 of the body 124, a peripheral edge 123 of the insert 125 coming into abutment on a peripheral edge 127 of the body 124.

The insert 125 defines a concave hemispherical surface $S_2$ with the same geometry as that of the prosthesis of the first form of embodiment.

The insert 125 is provided with a notch 128 at the level of its edge 123, while the body 124 bears a lug 129 on its edge 127. The cooperation of elements 128 and 129 makes it possible to immobilize the insert 125 in rotation about an axis $X_2$-$X'_2$ of the surface $S_2$.

Furthermore, the part 121 is added on an anchoring stem 122 intended to be immobilized in the humeral medullary canal. To that end, the body 124 is provided with an extension 124a intended to be introduced and wedged inside a housing 122a of corresponding shape provided in the stem 122.

As previously, the fact of making the surfaces $S_1$ and $S_2$ in parts 113 and 125 which are metallic makes it possible to improve the compactness of the prosthesis, while allowing easy, high-amplitude movements of the patient's arm with respect to the glenoid cavity.

According to an aspect of the invention (not shown), inserts 125 of different shapes may be provided to be mounted on the body 124, this making it possible to adapt the prosthesis to its site of implantation. For example, inserts 125 whose surfaces $S_2$ have different radii of curvature may be used, one of them being selected and mounted on the body 124 as a function of the geometry of the surface $S_1$ used for the glenoidal component. Similarly, inserts in which the surfaces $S_2$ are positioned differently with respect to the edge 123 may be used, one of them being selected, when installing the prosthesis, as a function of the patient's morphology.

The characteristics of the forms of embodiment described may be combined together within the scope of the present invention. In particular, a one-piece metaphyseal part, such as that of the first embodiment, may be added on an anchoring stem such as that of the second embodiment. Similarly, the body of the second embodiment may be in one piece with an anchoring stem, as in the first embodiment.

What is claimed is:

1. A total shoulder prosthesis comprising:
    a glenoid component including a metal convex articular surface, the glenoid component adapted for implantation proximate a glenoid cavity;
    a humeral component comprising a stem portion and a metaphyseal portion, the metaphyseal portion comprising a recess surrounded by a peripheral edge;
    a first insert comprising a first metal concave articular surface adapted to cooperate with the convex articular surface of the glenoid component, at least a portion of the first metal concave articular surface located within the recess when engaged with the metaphyseal portion, the metal concave articular surface on the first insert comprising a first configuration with respect to the metaphyseal portion;
    a second insert comprising a second metal concave articular surface adapted to cooperate with the convex articular surface of the glenoid component, at least a portion of the second metal concave articular surface located within the recess when engaged with the metaphyseal portion, the metal concave articular surface on the second insert comprising a second configuration with respect to the metaphyseal portion, wherein the first configuration is different from the second configuration; and
    a first feature on a peripheral edge of at least one of the inserts and a second feature provided on a top surface of the peripheral edge of the metaphyseal portion, the first and second features cooperating to immobilize the inserts from rotating relative to the metaphyseal portion.

2. The prosthesis of claim 1 wherein the humeral component comprises a monolithic structure.

3. The prosthesis of claim 1, wherein the first insert comprises a peripheral edge surrounding the first metal concave articular surface, the peripheral edge of the first insert abutting the peripheral edge of the metaphyseal portion when the first insert is engaged with the recess.

4. The prosthesis of claim 1 comprising a plurality of inserts each positioning the metal concave articular surface in a different configuration with respect to the metaphyseal portion.

5. The prosthesis of claim 1 wherein the location of the first insert relative to the peripheral edge of the metaphyseal portion comprises the first configuration, and the location of the second insert relative to the peripheral edge of the metaphyseal portion comprises the second configuration.

6. The prosthesis of claim 1 wherein at least the first metal concave articular surface is eccentric relative to the peripheral edge of the metaphyseal portion.

7. The prosthesis of claim 1 wherein the relative positions of the metaphyseal portion and the glenoid component are different in the first and second configurations.

8. The prosthesis of claim 1 comprising a third insert with a third metal concave articular surface adapted to cooperate with the convex articular surface of the glenoid component, the third metal concave articular surface comprising a third configuration with respect to the metaphyseal portion.

9. A method of implanting a total shoulder prosthesis comprising the steps of:
    implanting a glenoid component with a metal convex articular surface proximate a glenoid cavity;
    providing a humeral component comprising stem portion and a metaphyseal portion, the metaphyseal portion comprising a recess surrounded by a peripheral edge;
    providing a first insert comprising a first metal concave articular surface adapted to cooperate with the convex articular surface of the glenoid component;
    engaging the first insert with the metaphyseal portion so that at least a portion of the first metal concave surface is located in the recess and such that a feature on a peripheral edge of the first insert cooperates with a corresponding feature on a top surface of a peripheral edge of the metaphyseal portion to immobilize the first insert from rotating relative to the metaphyseal portion and wherein the first metal concave surface on the first insert comprises a first configuration with respect to the metaphyseal portion;

engaging a first metal concave articular surface on the first insert with the convex articular surface of the glenoid component;

substituting a second metal insert for the first metal insert on the humeral component;

engaging a second metal concave articular surface on the second insert with the convex articular surface of the glenoid component, the metal concave articular surface on the second insert comprising a second configuration with respect to the metaphyseal portion;

determining which of the first and second configurations most closely matches a patient's morphology; and implanting the stem portion so that one of the inserts is engaged with the metaphyseal component and the glenoid component.

10. The method of claim 9, wherein the humeral component comprises a monolithic structure.

11. The method of claim 9 comprising abutting a peripheral edge of the first insert against the peripheral edge of the metaphyseal portion when the first insert is engaged with the recess.

12. The method of claim 9 comprising a plurality of inserts each positioning the metal concave articular surface in a different configuration with respect to the metaphyseal portion.

13. The method of claim 9 wherein the location of the first insert relative to the peripheral edge of the metaphyseal portion comprises the first configuration, and the location of the second insert relative to the peripheral edge of the metaphyseal portion comprises the second configuration.

14. The method of claim 9 wherein at least the first metal concave articular surface is eccentric relative to the peripheral edge of the metaphyseal portion.

15. The method of claim 9 wherein the relative positions of the metaphyseal portion and the glenoid component are different in the first and second configurations.

16. A total shoulder prosthesis comprising:
a glenoid component including a metal convex articular surface, the glenoid component adapted for implantation proximate a glenoid cavity;
a monolithic humeral component comprising a stem portion and a metaphyseal portion, the metaphyseal portion comprising a recess surrounded by a peripheral edge;
a first insert comprising a first metal concave articular surface adapted to cooperate with the convex articular surface of the glenoid component, at least a portion of the first metal concave articular surface located within the recess when engaged with the metaphyseal portion, the first metal concave articular surface on the first insert comprising a first configuration with respect to the metaphyseal portion;
a second insert comprising a second metal concave articular surface adapted to cooperate with the convex articular surface of the glenoid component, the second metal concave articular surface comprising a second configuration, wherein the first configuration is different from the second configuration; and
a first feature on a peripheral edge of at least one of the inserts and a second feature provided on a top surface of the peripheral edge of the metaphyseal portion, the first and second features cooperating to immobilize the inserts from rotating relative to the metaphyseal portion.

17. The prosthesis of claim 16 further comprising a plurality of inserts, each comprising a metal concave articular surface having a different configuration with respect to the metaphyseal portion.

18. The prosthesis of claim 16 wherein a location of the first insert relative to the peripheral edge of the metaphyseal portion comprises the first configuration, and a location of the second insert relative to the peripheral edge of the metaphyseal portion comprises the second configuration.

19. The prosthesis of claim 16, wherein at least the first metal concave articular surface is eccentric relative to the peripheral edge of the metaphyseal portion.

20. A method of implanting a total shoulder prosthesis comprising the steps of:
implanting a glenoid component with a metal convex articular surface proximate a glenoid cavity;
providing a monolithic humeral component comprising a stem portion and a metaphyseal portion, the metaphyseal portion comprising a recess surrounded by a peripheral edge;
providing a first insert comprising a first metal concave articular surface adapted to cooperate with the convex articular surface of the glenoid component;
engaging the first insert with the metaphyseal portion so that at least a portion of a first metal concave articular surface is located in the recess such that a feature on a peripheral edge of the first insert cooperates with a corresponding feature on a top surface of a peripheral edge of the metaphyseal portion to immobilize the first insert from rotating relative to the metaphyseal portion, the first metal concave articular surface comprising a first configuration with respect to the metaphyseal portion;
engaging the first metal concave articular surface of the first insert with the convex articular surface of the glenoid component;
substituting a second insert for the first insert on the humeral component;
engaging a second metal concave articular surface on the second insert with the convex articular surface of the glenoid component, the second metal concave articular surface of the second insert comprising a second configuration with respect to the metaphyseal portion;
determining which of the first and second configurations most closely matches a patient's morphology; and
implanting the stem portion so that one of the inserts is engaged with the metaphyseal component and the glenoid component.

21. A total shoulder prosthesis comprising:
a glenoid component including a metal convex articular surface, the glenoid component adapted for implantation proximate a glenoid cavity;
a monolithic humeral component comprising a stem portion and a metaphyseal portion, the metaphyseal portion comprising a recess surrounded by a peripheral edge;
a first insert comprising a first metal concave articular surface adapted to cooperate with the convex articular surface of the glenoid component, at least a portion of the first metal concave articular surface located within the recess when engaged with the metaphyseal portion;
a second insert comprising a second metal concave articular surface adapted to cooperate with the convex articular surface of the glenoid component, at least a portion of the second metal concave articular surface located within the recess when engaged with the metaphyseal portion, the second metal concave articular surface comprising a second configuration with respect to the metaphyseal portion, wherein the first configuration is different from the second configuration; and a first feature on a top peripheral edge facing the glenoid component of at least one of the inserts and a second feature provided on a top surface of the peripheral edge of the metaphyseal portion, the first and second features cooperating to immobilize the inserts from rotating relative to the metaphyseal portion.

22. The prosthesis of claim 21 wherein the first insert comprises a peripheral edge surrounding the first metal concave articular surface, the peripheral edge of the first insert abutting the peripheral edge of the metaphyseal portion when the first insert is engaged with the recess.

23. The prosthesis of claim 21 further comprising a plurality of inserts, each comprising a metal concave articular surface having a different configuration with respect to the metaphyseal portion.

24. The prosthesis of claim 21 wherein a location of the first insert relative to the peripheral edge of the metaphyseal portion comprises the first configuration, and a location of the second insert relative to the peripheral edge of the metaphyseal portion comprises the second configuration.

25. The prosthesis of claim 21 wherein at least the first metal concave articular surface is eccentric relative to the peripheral edge of the metaphyseal portion.

26. The prosthesis of claim 21 wherein the relative positions of the metaphyseal portion and the glenoid component are different in the first and second configurations.

27. The prosthesis of claim 21 further comprising a third insert with a third metal concave articular surface adapted to cooperate with the convex articular surface of the glenoid component, the third metal concave articular surface comprising a third configuration with respect to the metaphyseal portion.

* * * * *

UNITED STATES PATENT AND TRADEMARK OFFICE
CERTIFICATE OF CORRECTION

| | |
|---|---|
| PATENT NO. | : 7,678,150 B2 |
| APPLICATION NO. | : 11/151658 |
| DATED | : March 16, 2010 |
| INVENTOR(S) | : Alain Tornier et al. |

It is certified that error appears in the above-identified patent and that said Letters Patent is hereby corrected as shown below:

Column 7

<u>Line 61</u>
After the word "portion", add -- , the first metal concave articular surface comprising a first configuration with respect to the metaphyseal portion --

Signed and Sealed this
Nineteenth Day of June, 2012

David J. Kappos
*Director of the United States Patent and Trademark Office*